(12) United States Patent
Surjadi et al.

(10) Patent No.: US 6,571,599 B1
(45) Date of Patent: Jun. 3, 2003

(54) AUTO-CALIBRATION OF PRESSURE TRANSDUCER OFFSET

(75) Inventors: Hary Soesanto Surjadi, Kariong (AU); Shane Darren Finn, North Rocks (AU); Gregory Alan Colla, North Sydney (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/500,853

(22) Filed: Feb. 9, 2000

Related U.S. Application Data

(62) Division of application No. 08/894,216, filed as application No. PCT/AU96/00413 on Jul. 3, 1996, now Pat. No. 6,237,592.

(30) Foreign Application Priority Data

Jul. 3, 1995 (AU) .............................................. PN3948

(51) Int. Cl.[7] .............................................. G01L 27/00
(52) U.S. Cl. ...................................................... 73/1.62
(58) Field of Search ................................ 73/1.62, 1.02; 600/532, 535, 538; 128/204.18

(56) References Cited

U.S. PATENT DOCUMENTS

| | | | |
|---|---|---|---|
| 3,903,875 A | 9/1975 | Hughes | 600/537 |
| 4,448,058 A | 5/1984 | Jaffe | 73/23.3 |
| 4,757,825 A * | 7/1988 | Diamond | 340/575 |
| 4,827,922 A | 5/1989 | Champain | 128/204.2 |
| 4,867,152 A * | 9/1989 | Kou et al. | 128/204.21 |
| 4,957,107 A | 9/1990 | Sipin | 128/204.2 |
| 5,117,819 A | 6/1992 | Servidio | 128/204.1 |
| 5,134,995 A | 8/1992 | Gruenke | 128/204.2 |
| 5,170,798 A | 12/1992 | Riker | 600/538 |
| 5,928,156 A * | 7/1999 | Krumbiegel et al. | 600/529 |

FOREIGN PATENT DOCUMENTS

| | | |
|---|---|---|
| EP | 0 425 092 A1 | 5/1991 |
| GB | 2 254 700 | 10/1992 |
| JP | 54-104369 | 8/1979 |

\* cited by examiner

*Primary Examiner*—Daniel S. Larkin
*Assistant Examiner*—Tamiko Bellamy
(74) *Attorney, Agent, or Firm*—Pillsbury Winthrop LLP

(57) ABSTRACT

A flow generator having use in the provision of CPAP or assisted ventilation treatment is disclosed The flow generator has a turbine for the supply of breathable gas which is driven by an electric motor and an associated motor power supply. The power supply in turn is controlled by a controller. A pressure sensing port measures delivery pressure that is passed to a pressure transducer, the output signal of which is passed to the motor controller. The zero offset of the pressure transducer is automatically calibrated on occurrence of the conditions where the turbine is not operating and no pressure activity is sensed by the transducer. The turbine not operating condition can be determined from Hall-effect sensors integral to the motor.

7 Claims, 6 Drawing Sheets

AUTO-CALIBRATION OF PRESSURE TRANSDUCER OFFSET

This application is a divisional of application Ser. No. 08/894,216 filed Feb. 3, 1998, now U.S. Pat. No. 6,237,592, which is a 371 of PCT/AU96/00413 filed Jul. 3, 1996, which is hereby incorporated by reference in its entirety.

FIELD OF THE INVENTION

This invention relates to the auto-calibration of pressure transducers. In one preferred form, it relates to pressure transducers for use in apparatus for the provision of Continuous Positive Airway Pressure (CPAP) treatment to patients suffering from obstructive Sleep Apnea (OSA) and for use in apparatus for ventilating assistance.

BACKGROUND OF THE INVENTION

CPAP is a well known treatment for the temporary relief of conditions including obstructive sleep apnea (OSA) and snoring. By this technique, air (or breathable gas) at a pressure elevated above atmospheric pressure is continuously supplied to the entrance of a patient's airway (by the nasal and/or oral route) by means of known arrangements of masks or nasal prongs. The elevated air pressure acts as a pneumatic splint of the patient's airway in the vicinity of the oro- and hypo-pharynx, reducing or eliminating the occurrences of apneas or hypopneas during sleep. A bi-level CPAP device, as opposed to a constant treatment level CPAP device, delivers two distinct pressures during the patient's respiratory cycle—a relatively lower pressure during exhalation and a relatively higher pressure during inhalation. In another form, an automatically adjusting CPAP device may operate to provide a relatively low background pressure which increases to a therapeutic pressure on a needs basis, and preferably at a time to prevent the onset of an apnea.

The term "CPAP" used herein thus is to be understood as including constant, bi-level or adjusting forms of continuous positive airway pressure.

Common to all forms of CPAP apparatus is a nose, mouth or face mask which is fitted to a patient and connected to a flow generator via a flexible air delivery tube/conduit. The flow generator includes an electric motor driving a turbine to provide a supply of air or breathable gas for the administration of CPAP treatment during sleep. The range of positive air pressures supplied at the entrance to a patient's airway typically is in the range 2–20 cm $H_2O$. In the pressure regulation control of the flow generator it is usual to have a continuous measure of mask or flow generator delivery pressure, commonly achieved by locating a pressure sensing port at the mask or proximate the flow generator outlet.

In the clinical assessment of the severity of a patient's OSA or upper airway syndrome condition, it is desired to identify the minimum possible CPAP treatment pressure that will alleviate the occurrence of partial or complete apneas during sleep. This is for the reason that the patient is required to expend respiratory effort in expiration against the positive airway pressure, hence it is preferable to minimise the work that must be done to ensure quality of sleep, and as follows administer only the minimal necessary CPAP treatment pressure. In this regard, it is important that the pressure transducer being used to measure the CPAP treatment pressure in control of the flow generator has satisfactory electromechanical characteristics so that the set-point CPAP treatment pressure does not vary significantly. It is known that a reduction of CPAP treatment pressure of as little as 1 cm $H_2O$ can nullify the therapeutic effect and result in a patient experiencing apneas during sleep.

There is, not unexpectantly, a direct correlation between the electro-mechanical performance of pressure transducers and price, hence the need for accurate pressure measurement is antagonistic towards the need to be able to manufacture CPAP apparatus at a cost that is acceptable to the marketplace. Commercially available pressure transducers, that are not extraordinarily expensive, operate in a small part of their pressure dynamic range in CPAP applications, meaning that there can be a 5–10% drift in the measured value with time due wholly to a pressure transducer operating in a 'stretched' region of operation. Such a variation translates to a variation in CPAP treatment pressure of about 1–2 cm $H_2O$. There further is market pressure for CPAP treatment to be determined to within an accuracy as low as 0.1 cm $H_2O$.

It is therefore one preferred object of the invention to be able to avoid the need to incorporate expensive pressure transducers in CPAP apparatus and yet still maintain accurate monitoring of, and control over, CPAP treatment pressure.

A similar consideration applies for ventilators or apparatus for assisted ventilation that provide breathable gas to a patient at a controlled pressure. The gas is delivered to the patient, in the case of a ventilator, by way of a mask or an endotracheal tube. Patients with lung disease, neuromuscular disease, chest wall disease, or abnormalities of respiratory control may require ventilatory assistance. This is because they have various combinations of elevated airway resistance, stiff lungs and chest wall, ineffective respiratory muscles, or insufficient neural activation of the respiratory muscles. The need for ventilatory assistance is particularly common during sleep. Pressure controlled, time triggered ventilators, for example, deliver a relatively high inspiratory pressure (IPAP) for a fixed period of time (TI), and a relatively low expiratory pressure (EPAP) for another fixed period of time (TE). The cycle is then repeated indefinitely.

Pressure transducers typically are factory calibrated before delivery, to establish a zero pressure value (with respect to CPAP treatment pressure that is relative to atmospheric pressure) in terms of the transducer's offset or bias. The "zero offset value" thus corresponds to atmospheric pressure. Even so, due to the inherent variations in the transduced pressure, and due to aging of the transducer and its temperature dependency, the preset offset value can vary by the equivalent of ±1 cm $H_2O$ leading to measurement error. This means that the patient must periodically return the CPAP apparatus to the manufacturer or servicer for re-calibration, else perform a re-calibration procedure themself, possibly requiring venting of the transducer to atmospheric pressure. It is therefore another preferred object of the invention to provide for auto-calibration of pressure transducer offset.

For convenience any reference to a "mask" hereafter is to be understood as including nasal, oral or face masks, and nasal prongs.

SUMMARY OF THE INVENTION

The present invention is directed to methods and apparatus whereby one or more of the foregoing problems can be overcome or at least ameliorated.

Therefore, in a broad form the invention discloses a method for auto-calibration of the offset of a pressure transducer for use in CPAP or pressure regulated ventilation apparatus, the CPAP apparatus comprising a flow generator operable to supply breathable gas to a delivery tube in turn connected to a patient mask, and the pressure transducer measuring delivery pressure in the mask, delivery tube or flow generator, the method comprising the steps of:

determining whether the flow generator is operating;

determining whether there is no pressure activity sensed by the transducer; and if both determinations are satisfied, accepting the output of the transducer as a calibrated pressure offset value representative of atmospheric pressure.

The invention further discloses a method for auto-calibration of the offset of a pressure transducer for use in CPAP or pressure regulated ventilation apparatus, the apparatus comprising a flow generator operable to supply breathable gas to a delivery tube in turn connected to a patient mask, and the pressure transducer measuring delivery pressure in the mask, delivery tube or flow generator, the method comprising the steps of:

determining whether no pressure activity is continuously sensed by the transducer over a predetermined period of time, and if so accepting the output of the transducer as a calibrated pressure offset value representative of atmospheric pressure.

The invention yet further discloses a flow generator for the supply of breathable gas comprising an electric motor driving a turbine, control circuitry, a pressure transducer to sense delivery pressure at or remote from said flow generator and whose electrical output is connected to said control circuitry, and sensing means connected to said control circuitry, and wherein said control circuitry is operable to determine from said sensing means whether the electric motor or the turbine are operating and from the pressure transducer whether there is no pressure activity, and if both determinations are satisfied, to accept the output of the transducer as a calibrated pressure offset value representative of atmospheric pressure.

The invention yet further discloses a flow generator for the supply of breathable gas comprising an electric motor driving a turbine, control circuitry, and a pressure transducer to sense delivery pressure at or remote from said flow generator and whose electrical output is connected to said control circuitry, and wherein said control circuitry is operable to determine from the pressure transducer whether there is no pressure activity continuously over a predetermined period of time, and if so, to accept the output of the transducer as a calibrated pressure offset value representative of atmospheric pressure.

An auto-calibration thus can be performed in the sense that there is no user/patient involvement nor manual activation, rather performance by the flow generator autonomously. If either determination is not met an auto-calibration is not performed.

The pressure offset value is applied to all subsequent pressure measurements to determine treatment pressure. Preferably, the two determinations are made over a plurality of successive instances and must both be satisfied on each instance before accepting the updated offset value.

In a preferred form, the current pressure value is compared against a preceding pressure value, and if differing less than a predetermined threshold then there is pressure inactivity. The preceding pressure value can be a running or moving average of such values.

The electric motor operation sensing means can be Hall-effect sensors integral of, or mounted to the electric motor. The flow generator can further comprise power supply means being controlled by the control circuitry and having control of the rotational speed of the electric motor.

The invention further discloses a flow generator as described, and a delivery tube coupled thereto and to a patient mask. The mask can be a nose, mouth or face mask. The pressure sensing port can be located at the turbine exit, a point along the tube or at the mask.

In one preferred form, the invention can be said to involve methods and apparatus for providing auto-calibration of pressure transducer offset that is implemented by continuously monitoring the flow generator electric motor to determine whether it is running and monitoring the pressure transducer for respiratory activity. If the motor is not running, and no pressure activity is detected, then the pressure measured by the transducer is determined to be atmospheric pressure, and so the electrical output from the transducer represents the zero pressure offset. The offset value at this point in time is stored to be subtracted from any subsequent pressure measurement values to determine treatment pressure.

In an alternate embodiment, auto-calibration of pressure transducer offset is implemented by determining whether there is no pressure activity sensed by the pressure transducer over a continuous period that is long compared with physiological events such as respiration and apnea. This single determination thus subsumes the separate determinations of motor operation and respiratory activity.

The zero offset can be updated whenever the opportunity arises, thus taking into account effects due to transducer ageing and temperature effects. In this way, the magnitude of a transducer's offset error can be determined automatically without the need for additional hardware elements, such as a solenoid-operated valve venting the transducer to atmospheric. There also is no need for any user intervention in the periodic recalibration. This leads to a reduction in the cost of the hardware components of a CPAP or pressure regulated ventilation apparatus, and to a reduced manufacturing unit cost due to a reduction in labour required, for reason of there being no need to manually calibrate a transducer at the factory in advance of shipment, in combination resulting in reduced cost of the apparatus to the patient.

The improved pressure measurement accuracy gained also has therapeutic benefit, in that the CPAP or ventilation treatment will remain effective for a patient, in that the clinically-determined delivery pressure is maintained with accuracy.

DESCRIPTION OF THE DRAWINGS

An embodiment of the invention now will be described with reference to the accompanying drawings, in which.

DETAILED DESCRIPTION OF PREFERRED EMBODIMENTS AND BEST MODE

The embodiment to be described relates to CPAP apparatus, however it is to be understood that other embodiments are equally applicable in the field of pressure regulated ventilators.

Figure 1:
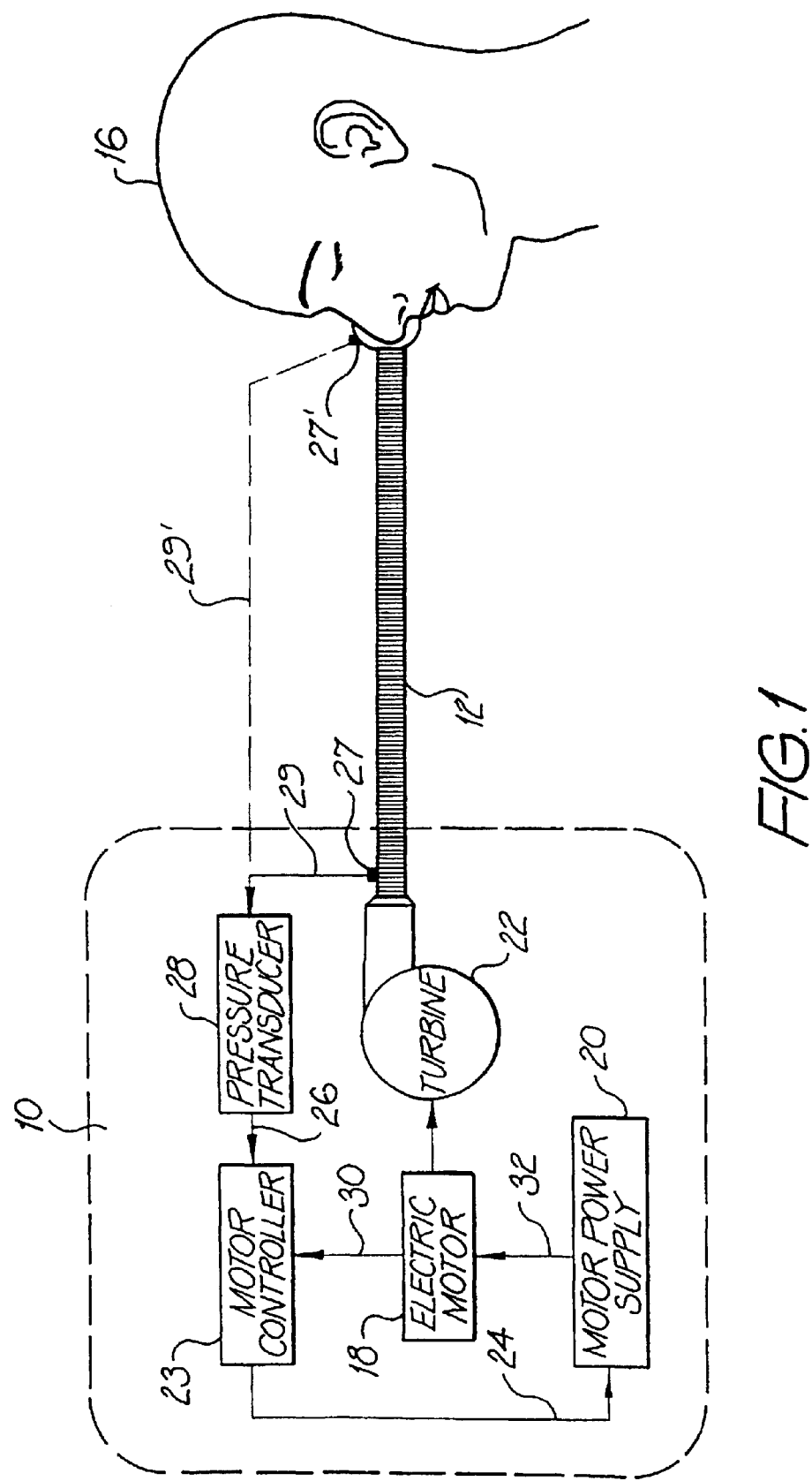
FIG. 1 is a schematic block diagram of CPAP apparatus as used for the treatment of OSA.

Referring then to FIG. 1, the CPAP apparatus comprises a flow generator 10 coupled by a flexible delivery tube or conduit 12, in this case, to a nose mask 14 worn by a patient 16. The flow generator 10 broadly comprises an electric motor 18 that is powered by a motor power supply 20. In turn, the electric motor 18 has mechanical coupling with a turbine 22 that outputs either air or breathable gas at a pressure elevated above atmospheric pressure to the delivery tube 12. The output delivery pressure from the turbine 22 is governed by the rotational speed of the electric motor 18. The speed thus is the "controlled variable" relative to the desired CPAP treatment pressure. The motor 18 speed is controlled by the motor controller 23 which effects changes in motor speed by means of a control signal on control line 24 provided to the motor power supply 20. Accordingly, motor speed is controlled by means of varying the motor power supply 20, typically in output voltage and/or duty cycle.

The motor controller 23 receives an electrical signal on control line 26 in this case representative of delivery pressure from the turbine 22 as measured by the pressure transducer 28, which is connected via a sensing line 29 to a sensing port 27 proximate to the turbine outlet. In an alternative form, the pressure transducer 28 can be connected via a sensing line 29' to a sensing port 27' located at the nose mask 14.

In the event of the transducer 28 being located at the turbine 22 outlet, it is necessary for the motor controller to be able to compensate for pressure losses (as a function of flow) along the delivery tube 12, since ultimately it is the pressure at the entrance to the airway that is to be monitored and controlled to ensure effective CPAP treatment. This compensation can be performed by empirical measurement or by a knowledge of the flow vs pressure characteristic of the delivery tube 12.

In one preferred form, the turbine 22 can be a PAPST™ ECA 27-11 brushless DC motor. Being a DC motor, its speed is directly proportional to the armature voltage. The particular motor described has integral Hall-effect sensors, thus providing a measure of motor angular rotational speed, that signal being output from the motor 18 to the motor controller 22 on control line 30.

The pressure transducer 28 can be such as a Motorola™ MPX 2010DP type. The motor controller 23 can be implemented by any commercially available microprocessor, although one preferred form is the 8-bit Motorola™ MC68HC805B6 micro-controller.

When the motor 18 is not running, hence the turbine 22 is not rotating to produce pressurised air or breathable gas, if the nose mask 14 is not being worn then the air pressure measured by the transducer 28 will be atmospheric pressure. The transducer 28 will have an electrical output in response only to atmospheric pressure. The measurement obtained of atmospheric pressure represents the "zero offset" value, and hence the motor controller 23 must be calibrated to take into account this zero offset so accurate measurements can be performed. That "zero offset" output must be subtracted from a pressure value measured with the turbine 22 rotating in order to obtain a measurement of CPAP delivery pressure.

As previously discussed, the electrical performance of pressure transducers varies over time, and whilst the linearity may remain essentially constant, the zero offset can vary by 5–10% The present embodiment operates to auto-calibrate the transducer in terms of the "zero offset" at available times, viz., occasions when the flow generator 10 is not being operated and the mask 14 is not being worn (or there is no respiration) by the patient 16.

Figure 2:
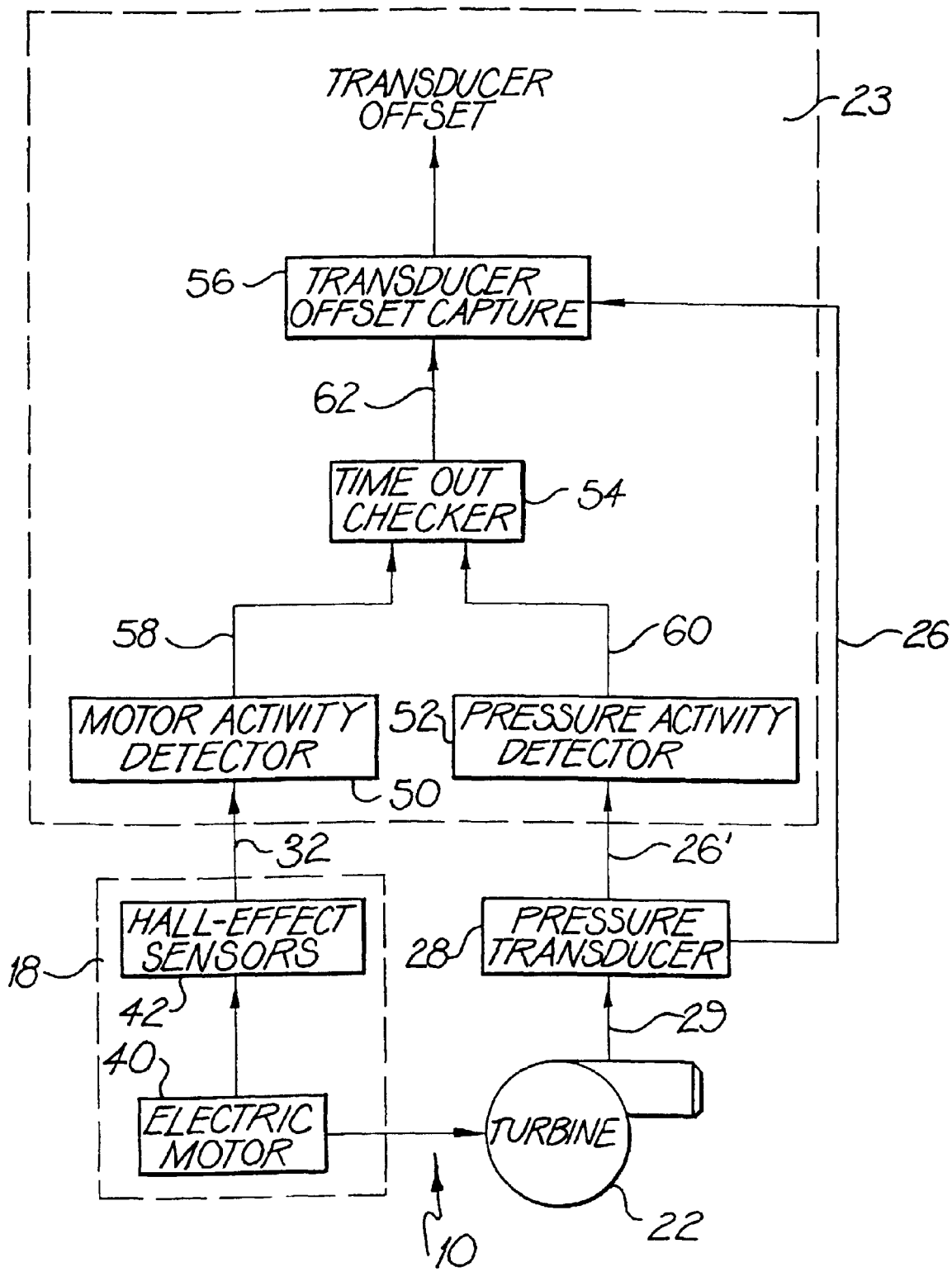
FIG. 2 is a schematic block diagram representative of hardware components constituting an embodiment of the invention.

In FIG. 2 the elements common with FIG. 1 are shown using like reference numerals. The electric motor 18 is represented by the component motor 40 and integral Hall-effect (speed) sensors 42. Within the dashed box representing the motor controller 23, only some number of the logic elements constituting the controller have been shown. These logic elements are the ones involved in generation of a "Transducer Offset" signal that equates to the "zero offset" value of the transducer and thus atmospheric pressure.

The output signal from the speed sensors 42 is passed on a control line 32 to a motor activity detector 50, and the signal representing the measured pressure appears on another control line 26 to be passed to a pressure activity detector 52. Both the motor activity detector 50 and the pressure activity detector 52 pass logic signals on respective lines 58, 60 to a time-out checker 54, the output from which is passed on a line 62 to a transducer offset capture element 56 that also receives the output of the pressure transducer 28. These two signals are processed to generate the "Transducer Offset" value to be passed to other processing elements of the motor controller 23.

Reference now will be made to the flow diagram of FIG. 3 and the logic and computational steps therein that further describe the present embodiment. These steps are performed by the motor controller 23 in the form of either a stored computer program in machine readable form or discrete logic elements. Step 60 determines whether a warm-up period has elapsed to allow the flow generator 10 to reach a normal operating temperature. A typical minimum warm-up time is 15 minutes. If this step is satisfied, the "pressure activity counter" is reset (i.e. to zero) in step 62, followed by step 64 that determines whether the motor 40 is operating/running. This step is performed through use of the Hall-effect sensors 42 and the motor activity detector 50. If the motor is running, it is not possible to perform the auto-calibration. If the motor is not running, step 66 determines whether any pressure activity is sensed. This is achieved by way of the pressure transducer 28 and the pressure activity detector 52. If there is pressure activity then again the auto-calibration cannot be performed. Pressure activity can be defined as an absolute difference between two consecutively measured pressure samples exceeding a predetermined threshold. In this regard the immediately preceding value is stored and compared with the current value. The difference is compared with a predetermined threshold, typically set to ±0.5% (approximately equivalent to 1 count in a range of 185 counts). If the threshold is not exceeded, it is determined there is no pressure activity.

If no pressure activity is sensed, then in step 68 the "pressure inactivity counter" is incremented. In step 68 the value of the pressure inactivity counter is compared against a "pressure inactive time-out" value (viz., by the time-out checker 54) that is implemented to ensure that there is a minimum duration of no motor activity and no pressure activity before auto-calibration can take place. Thus the tests of steps 64 and 66 must be satisfied more than once in the looped-manner shown before the test of step 70 will be satisfied and, as indicated in step 72, the current pressure transducer output is captured and utilised as an auto-calibration of the Transducer Offset.

The pressure inactive time-out value preferably may be a number of interactions equivalent to, say, a two second duration.

The absence of pressure activity corresponds to the absence of respiration, which, in most every case, will be due to the mask 14 not being worn. The only practical instance of there being a lack of pressure activity with the mask being worn is if the patient has ceased breathing, whether that is a consequence of occurrence of an apnea or otherwise. In any event, it would be even rarer for a patient to be wearing a mask during sleep without the electric motor 40 operating.

The "motor not running" condition and the "mask not being worn" condition will tend to occur when the flow generator 10 is first turned on, or may arise from the patient stopping the flow generator, or the flow generator automatically stopping itself in the presence of sensing 'mask off' (whether that be intentional or otherwise).

By the methodology described, the Transducer Offset can be updated every two seconds (for example) when the motor 40 is not operating and the mask is not being worn, in that these conditions are satisfied many times over before the time-out period elapses, but only the pressure value immediately preceding the end of the time out period is captured as the updated Transducer Offset.

In other embodiments it may be preferred to utilise a running or moving average of previous (say, at least five) pressure samples compared with the current pressure sample to determine whether there is pressure inactivity. Such averaging functions can be achieved by the introduction of appropriate software or hardware filters.

In a further embodiment, it may be chosen to base the auto-calibrating Transducer Offset value not upon the instantaneous (atmospheric) sensed pressure, but upon some averaged representation of sensed pressure over a contemporaneous historical period.

In a yet further embodiment, it may also be chosen to separately store the transducer offset measured prior to satisfying the warm-up condition in step 60 so that both a "cold-offset" and a "warm-offset" are stored.

Figure 4:
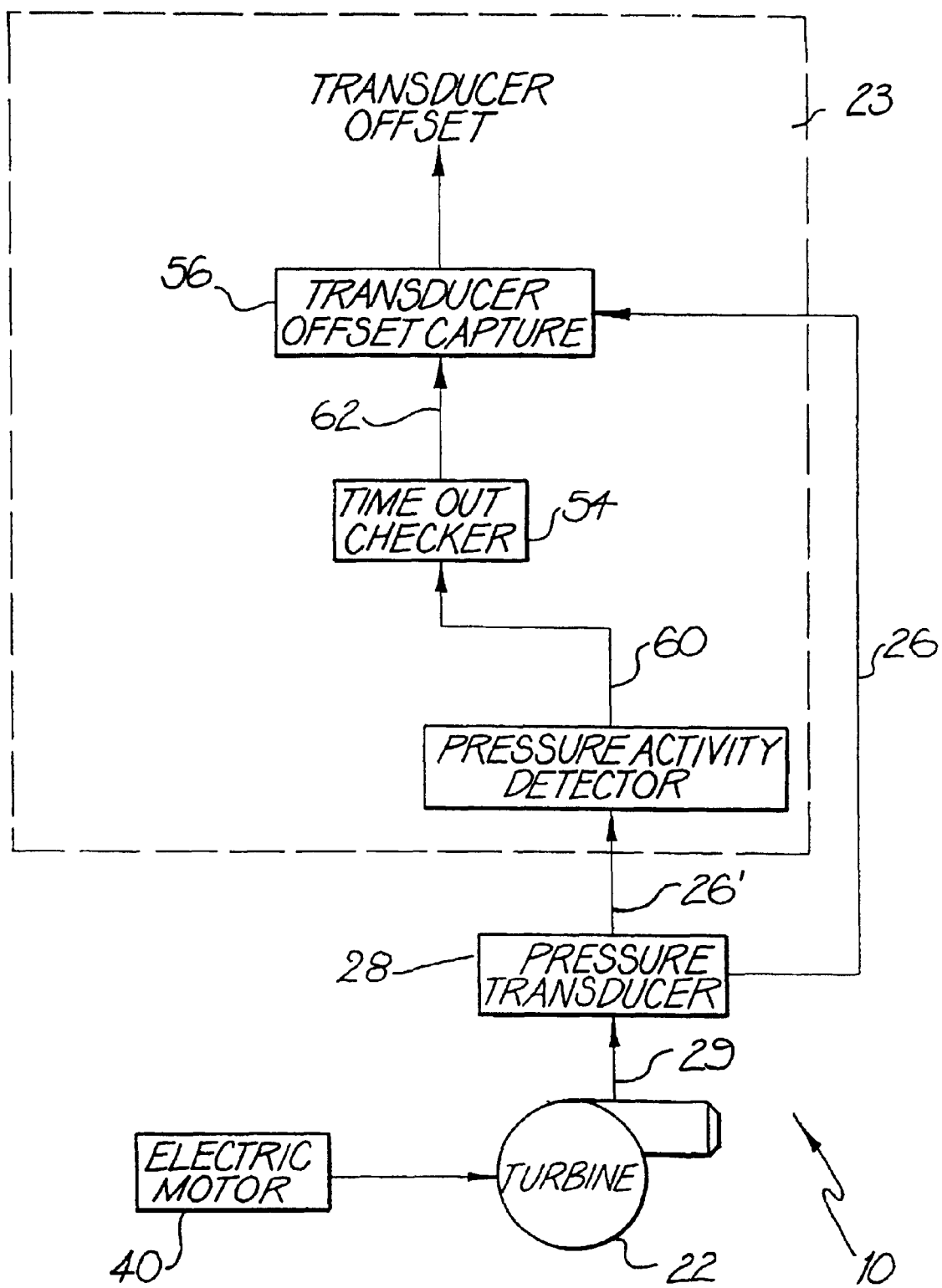
FIG. 4 is a schematic block diagram representative of hardware components constituting another embodiment.
Figure 5:
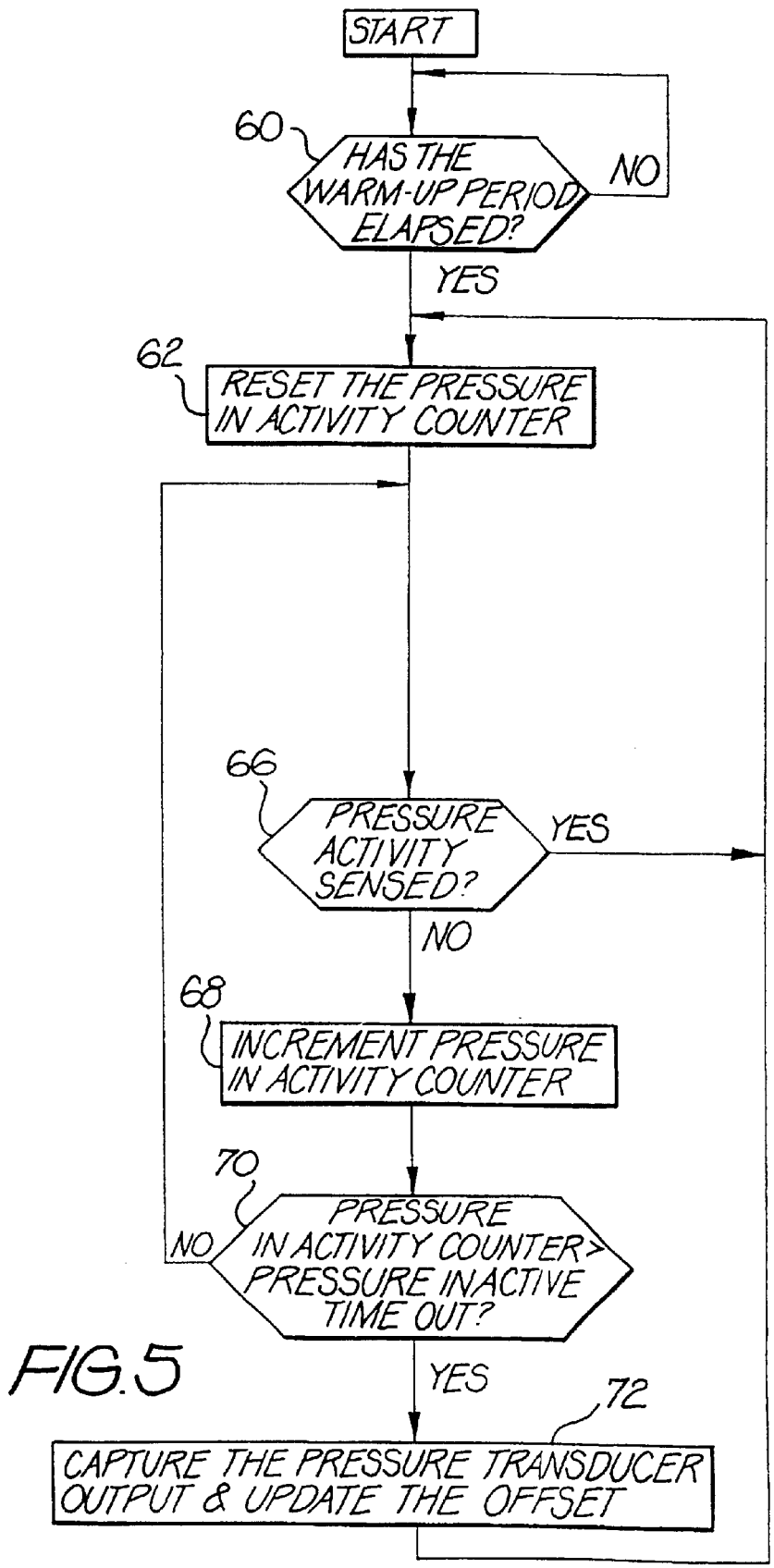
FIG. 5 is a schematic block diagram of representative computational steps in performance of another embodiment.

An alternative embodiment is shown with reference to FIGS. 4 and 5. In this embodiment the determination of whether the flow generator 10 is in a condition such that auto-calibration can take place occurs on the basis only of the pressure measured by the pressure transducer 28. That is, a determination of the CPAP mask not being worn and the turbine 22 not operating can be arrived at based only on the pressure measurement.

Figure 3:
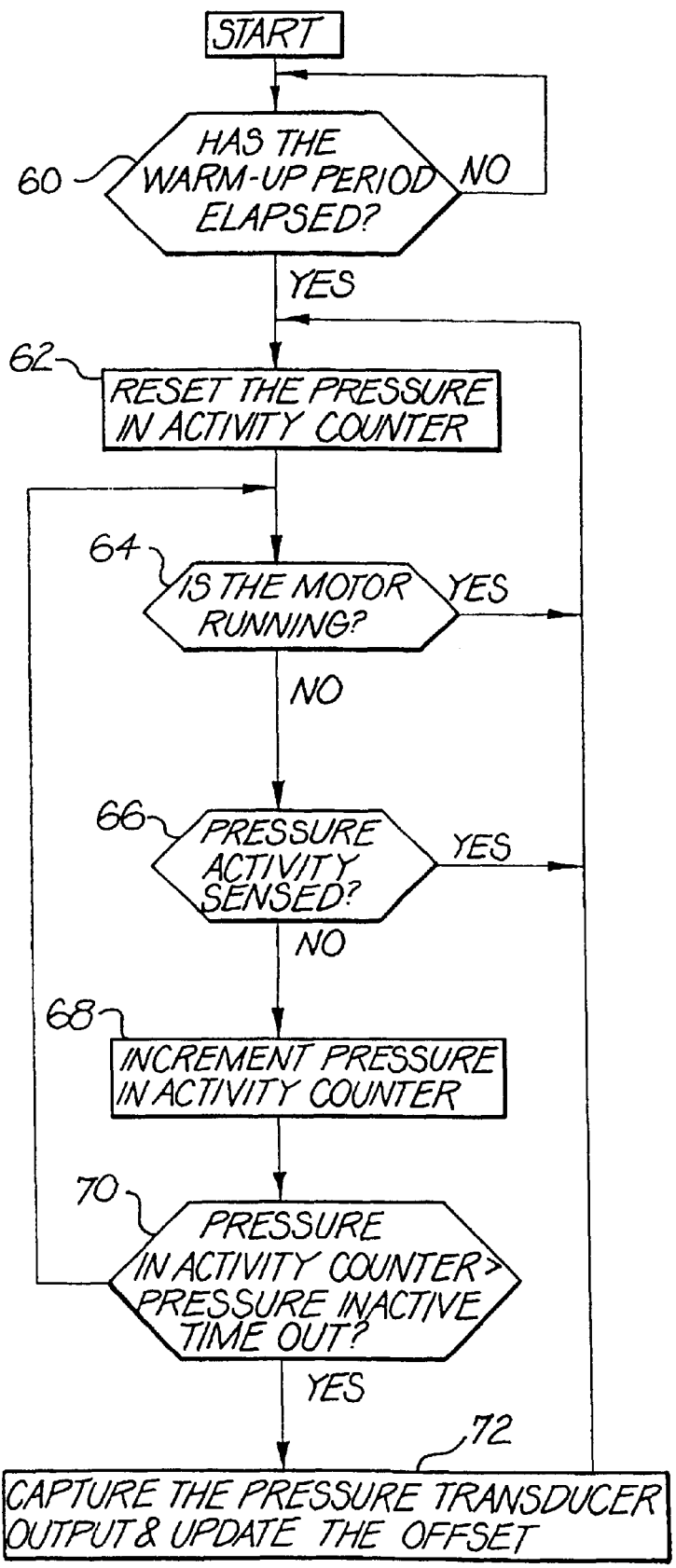
FIG. 3 is a schematic block diagram of representative computational steps in performance of the embodiment.

The steps shown in FIG. 5 are common with the steps previously shown in FIG. 3, but for omission of the "motor running" step 64. The other difference occurs in relation to step 70, inasmuch as the "time out" value is set to be long with respect to any physiological event. Typical physiological events are respiration and apneas. A time out period of between 2–5 minutes has been determined to be satisfactory.

In the event that a patient mask is not being worn and the electric motor 40 is operating to cause rotation of the turbine 22, then for reasons of the flow of air past the mask the pressure transducer 28 to be discharged from the mask into free space, it is the case that fluctuations or perturbations in pressure will be sensed by the pressure transducer 28 to even to fluid dynamics effects in the physical vicinity of the pressure transducer 28. A minimum threshold of 0.1 cm $H_2O$ can be utilised to discriminate between pressure activity and pressure inactivity.

Figure 6:
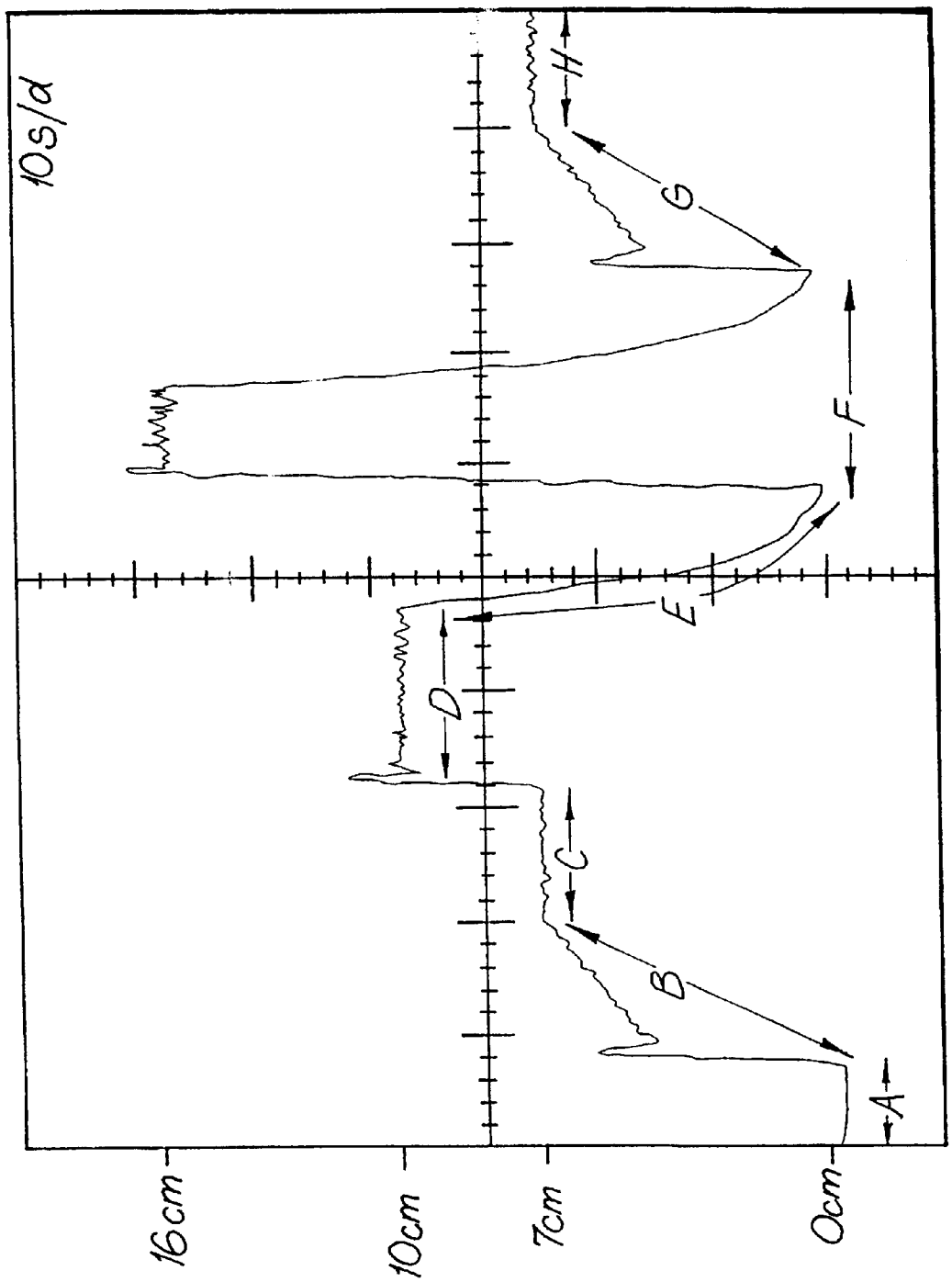
FIG. 6 shows a typical pressure waveform during calibration.

FIG. 6 shows a waveform of pressure versus time for the embodiment of FIGS. 2 and 3, where the time axis is in 10 seconds per division increments. The waveform represents the signal measured by the pressure transducer 28 with the internal pressure offset applied to provide relative treatment pressure. Time interval A represents the situation of the flow generator 10 being turned off, in which case the measured pressure is 0 cm $H_2O$ relative to atmospheric pressure. Time interval B represents the flow generator stepping up to the minimum CPAP pressure of 4 cm $H_2O$ then ramping to the target treatment pressure of 7 cm $H_2O$. Time interval C represents continuous operation at the desired treatment pressure. At the end of time interval C, an artificial offset error is introduced so that the actual pressure generated is 10 cm $H_2O$ whereas the flow generator believes the delivery pressure is 7 cm $H_2O$. Thus a 3 cm $H_2O$ error in the transducer offset has been introduced. Time interval D represents the continuing operational period with the error in transducer offset. At the end of interval D the flow generator is turned off, and in interval E, the pressure reduces to 0 cm $H_2O$.

In time interval F two calibration operations are performed. Immediately at the commencement of the interval (upon turning on of the flow generator), the pressure transducer offset value is recalibrated given that the two conditions of the flow generator not operating and there being no pressure activity are satisfied. What follows is a period in which the flow generator operates at approximately 15 cm $H_2O$, this being a gain calibration that is not directly applicable to the present invention. After the gain calibration, the flow generator again turns off, with the pressure returning to the 0 cm $H_2O$ level. Time interval G represents a ramping-up to resumption of CPAP treatment in interval H at the now correct delivery pressure level of 7 cm $H_2O$.

What is claimed is:

1. A method for auto-calibration of the offset of a pressure transducer for use in CPAP or pressure regulated ventilation apparatus, the apparatus comprising a flow generator operable to supply breathable gas to a delivery tube in turn connected to a patient mask, and the pressure transducer measuring delivery pressure in the mask, delivery tube or flow generator, the method comprising:

determining whether the flow generator is not operating;
   determining whether there is no pressure activity sensed by the transducer; and
   if both determinations are satisfied, accepting the output of the transducer as a calibrated pressure offset value representative of atmospheric pressure.

2. A method as claimed in claim 1, whereby said no pressure activity is determined by determining whether there is no absolute difference between two consecutive measurements of pressure by the pressure transducer.

3. A method as claimed in claim 2, whereby said no absolute difference between two consecutive measurements of pressure is determined by comparing a stored immediately preceding measured pressure value with a current pressure value, comparing the difference against a threshold, and if the threshold is not exceeded, there is no pressure activity.

4. A method as claimed in any one of claims 1 to 3, whereby said flow generator not operating is determined by detecting near zero rotational speed of the flow generator.

5. A method as claimed in any one of claims 1 to 3, whereby said flow generator not operating is determined by there being no sensed pressure activity over a continuous period of time that is long compared with any physiological event.

6. A method for auto-calibration of the offset of a pressure transducer for use in CPAP or pressure regulated ventilation apparatus, the apparatus comprising a flow generator operable to supply breathable gas to a delivery tube in turn connected to a patient mask, and the pressure transducer measuring delivery pressure in the mask, delivery tube or flow generator, the method comprising:

determining whether no pressure activity is continuously sensed by the transducer over a predetermined period of time, and if so accepting the output of the transducer as a calibrated pressure offset value representative of atmospheric pressure.

7. A method as claimed in claim 6, whereby the period of time is long compared with any physiological event.

* * * * *

UNITED STATES PATENT AND TRADEMARK OFFICE
CERTIFICATE OF CORRECTION

PATENT NO. : 6,571,599 B1
DATED : June 3, 2003
INVENTOR(S) : Surjadi et al.

It is certified that error appears in the above-identified patent and that said Letters Patent is hereby corrected as shown below:

Title page,
Item [56], References Cited, insert:

| U.S. PATENT DOCUMENTS | | |
|---|---|---|
| RE 35,295 | 7/1996 | Estes et al. |
| RE 35,339 | 10/1996 | Rapoport |
| 2,904,033 | 9/1959 | Shane |
| 3,099,985 | 8/1963 | Wilson et al. |
| 3,502,100 | 3/1970 | Jonson |
| 3,559,638 | 2/1971 | Potter |
| 3,595,228 | 7/1971 | Simon et al. |
| 3,611,801 | 10/1971 | Paine et al. |
| 3,726,270 | 4/1973 | Griffis et al. |
| 3,741,208 | 6/1973 | Jonsson et al. |
| 3,783,893 | 1/1974 | Davison |
| 3,802,417 | 4/1974 | Lang |
| 3,817,246 | 6/1974 | Weigl |
| 3,882,847 | 5/1975 | Jacobs |
| 3,903,875 | 9/1975 | Hughes |
| 3,914,994 | 10/1975 | Banner |
| 3,932,054 | 1/1976 | McKelvey |
| 3,985,467 | 10/1976 | Lefferson |
| 3,989,037 | 11/1976 | Franetzki |
| 3,992,598 | 11/1976 | Welsh et al. |
| 3,995,661 | 12/1976 | Van Fossen |
| 4,006,634 | 2/1977 | Billette et al. |
| 4,083,245 | 4/1978 | Osborn |
| 4,109,749 | 8/1978 | Sweet |
| 4,119,096 | 10/1978 | Drews |
| 4,206,754 | 6/1980 | Cox et al. |
| 4,249,527 | 2/1981 | Ko et al. |
| 4,301,833 | 11/1981 | Donald, III |
| 4,312,235 | 1/1982 | Daigle |
| 4,322,594 | 3/1982 | Brisson |
| 4,381,788 | 5/1983 | Douglas |
| 4,387,722 | 6/1983 | Kearns |
| 4,396,034 | 8/1983 | Cherniak |
| 4,414,982 | 11/1983 | Durkan |
| 4,433,693 | 2/1984 | Hochstein |
| 4,448,058 | 5/1984 | Jaffe |
| 4,481,944 | 11/1984 | Bunnell |
| 4,449,525 | 5/1984 | White et al. |
| 4,499,914 | 2/1985 | Schebler |
| 4,506,666 | 3/1985 | Durkan |
| 4,519,399 | 5/1985 | Hori |
| 4,550,615 | 11/1985 | Grant |
| 4,550,726 | 11/1985 | McEwen |
| 4,558,710 | 12/1985 | Eichler |
| 4,570,631 | 2/1986 | Durkan |
| 4,579,114 | 4/1986 | Gray et al. |
| 4,580,575 | 4/1986 | Birnbaum et al. |
| 4,592,880 | 6/1986 | Murakami |
| 4,595,016 | 6/1986 | Fertig et al. |
| 4,602,644 | 7/1986 | DiBenedetto et al. |
| 4,630,614 | 12/1986 | Atlas |
| 4,648,396 | 3/1987 | Raemer |
| 4,648,407 | 3/1987 | Sackner |
| 4,665,213 | 4/1987 | Rapoport et al. |
| 4,667,975 | 7/1987 | Edgar et al. |
| 4,686,974 | 8/1987 | Sato et al. |
| 4,686,999 | 8/1987 | Snyder et al. |
| 4,738,266 | 4/1988 | Thatcher |

UNITED STATES PATENT AND TRADEMARK OFFICE
CERTIFICATE OF CORRECTION

PATENT NO. : 6,571,599 B1
DATED : June 3, 2003
INVENTOR(S) : Surjadi et al.

It is certified that error appears in the above-identified patent and that said Letters Patent is hereby corrected as shown below:

Title page (cont'd),

| | | |
|---|---|---|
| 4,747,403 | 5/1988 | Gluck et al. |
| 4,757,825 | 7/1988 | Diamond |
| 4,773,411 | 9/1988 | Downs |
| 4,777,963 | 10/1988 | McKenna |
| 4,795,314 | 1/1989 | Prybella et al. |
| 4,802,485 | 2/1989 | Bowers et al. |
| 4,803,471 | 2/1989 | Rowland |
| 4,819,629 | 4/1989 | Jonson |
| 4,823,788 | 4/1989 | Smith et al. |
| 4,825,802 | 5/1989 | Le Bec |
| 4,827,922 | 5/1989 | Champain et al. |
| 4,838,258 | 6/1989 | Dryden et al. |
| 4,844,085 | 7/1989 | Gattinoni |
| 4,856,506 | 8/1989 | Jinotti |
| 4,860,766 | 8/1989 | Sackner |
| 4,867,152 | 9/1989 | Kou et al. |
| 4,870,960 | 10/1989 | Hradek |
| 4,870,963 | 10/1989 | Carter |
| 4,913,401 | 4/1990 | Handke |
| 4,915,103 | 4/1990 | Visveshwara et al. |
| 4,928,684 | 5/1990 | Breitenfelder et al. |
| 4,938,210 | 7/1990 | Shene |
| 4,938,212 | 7/1990 | Snook et al. |
| 4,944,310 | 7/1990 | Sullivan |
| 4,957,107 | 9/1990 | Sipin |
| 4,960,118 | 10/1990 | Pennock |
| 4,971,065 | 11/1990 | Pearce |
| 4,972,842 | 11/1990 | Korten et al. |
| 4,982,738 | 1/1991 | Griebel |
| 4,986,269 | 1/1991 | Hakkinen |
| 4,989,599 | 2/1991 | Carter |
| 5,009,635 | 4/1991 | Scarberry |
| 5,024,219 | 7/1991 | Dietz |
| 5,046,491 | 9/1991 | Derrick |
| 5,048,515 | 9/1991 | Sanso |
| 5,052,400 | 10/1991 | Dietz |
| 5,063,922 | 11/1991 | Hakkinen |
| 5,063,938 | 11/1991 | Beck et al. |
| 5,065,756 | 11/1991 | Rapoport |
| 5,069,222 | 12/1991 | McDonald, Jr. |
| 5,099,837 | 3/1992 | Russel Sr. et al. |
| 5,105,354 | 4/1992 | Nishimura |
| 5,107,830 | 4/1992 | Younes |
| 5,107,831 | 4/1992 | Halpern et al. |
| 5,117,819 | 6/1992 | Servidio |
| 5,129,390 | 7/1992 | Chopin et al. |
| 5,134,995 | 8/1992 | Gruenke et al. |
| 5,148,802 | 9/1992 | Sanders et al. |
| 5,161,525 | 11/1992 | Kimm et al. |
| 5,161,541 | 11/1992 | Bowman et al. |
| 5,165,398 | 11/1992 | Bird |
| 5,170,798 | 12/1992 | Riker |
| 5,174,287 | 12/1992 | Kallok et al. |
| 5,178,138 | 1/1993 | Walstrom et al. |
| 5,190,048 | 3/1993 | Wilkinson |
| 5,183,983 | 2/1993 | Knop |
| 5,195,528 | 3/1993 | Hok |
| 5,199,424 | 4/1993 | Sullivan et al. |
| 5,203,343 | 4/1993 | Axe et al. |
| 5,230,330 | 7/1993 | Price |

UNITED STATES PATENT AND TRADEMARK OFFICE
CERTIFICATE OF CORRECTION

PATENT NO. : 6,571,599 B1
DATED : June 3, 2003
INVENTOR(S) : Surjadi et al.

It is certified that error appears in the above-identified patent and that said Letters Patent is hereby corrected as shown below:

Title page (cont'd),

| | | |
|---|---|---|
| 5,231,979 | 8/1993 | Rose et al. |
| 5,231,983 | 8/1993 | Matson et al. |
| 5,239,994 | 8/1993 | Atkins |
| 5,239,995 | 8/1993 | Estes et al. |
| 5,245,995 | 9/1993 | Sullivan et al. |
| 5,259,373 | 11/1993 | Gruenke et al. |
| 5,271,391 | 12/1993 | Graves |
| 5,280,784 | 1/1994 | Kohler |
| 5,293,864 | 3/1994 | McFadden |
| 5,303,698 | 8/1994 | Tobia et al. |
| 5,303,700 | 4/1994 | Weismann et al. |
| 5,305,787 | 4/1994 | Thygesen |
| 5,311,875 | 5/1994 | Stasz |
| 5,313,937 | 5/1994 | Zdrojkowski |
| 5,322,057 | 6/1994 | Raabe et al. |
| 5,335,654 | 8/1994 | Rapoport |
| 5,335,656 | 8/1994 | Bowe et al. |
| 5,343,878 | 9/1994 | Scarberry et al. |
| 5,353,788 | 10/1994 | Miles |
| 5,360,008 | 11/1994 | Campbell, Jr. |
| 5,373,842 | 12/1994 | Olsson et al. |
| 5,388,571 | 2/1995 | Roberts et al. |
| 5,394,882 | 3/1995 | Mawhinney |
| 5,398,673 | 3/1995 | Lambert |
| 5,400,777 | 3/1995 | Olsson et al. |
| 5,404,871 | 4/1995 | Goodman et al. |
| 5,413,111 | 5/1995 | Wilkinson |
| 5,443,061 | 8/1995 | Champain et al. |
| 5,443,075 | 8/1995 | Holscher |
| 5,433,193 | 7/1995 | Sanders et al. |
| 5,438,980 | 8/1995 | Phillips |
| 5,443,061 | 08/1995 | Champain et al. |
| 5,458,137 | 10/1995 | Axe et al. |
| 5,479,920 | 1/1996 | Piper et al. |
| 5,483,969 | 1/1996 | Testerman et al. |
| 5,492,113 | 2/1996 | Estes et al. |
| 5,490,502 | 2/1996 | Rapoport et al. |
| 5,503,146 | 4/1996 | Froehlich et al. |
| 5,507,282 | 4/1996 | Younes |
| 5,509,404 | 4/1996 | Lloyd et al. |
| 5,509,414 | 4/1996 | Hok |
| 5,513,631 | 5/1996 | McWilliams |
| 5,517,983 | 5/1996 | Deighan et al. |
| 5,522,382 | 6/1996 | Sullivan et al. |
| 5,526,805 | 6/1996 | Lutz et al. |
| 5,535,738 | 7/1996 | Estes et al. |
| 5,535,739 | 7/1996 | Rapoport et al. |
| 5,537,997 | 7/1996 | Mechlenburg et al. |
| 5,540,219 | 7/1996 | Mechlenburg et al. |
| 5,540,220 | 7/1996 | Gropper |
| 5,540,733 | 7/1996 | Testerman et al. |
| 5,546,933 | 8/1996 | Rapoport et al. |
| 5,546,952 | 8/1996 | Erickson |
| 5,549,106 | 8/1996 | Gruenke et al. |
| 5,549,555 | 8/1996 | Erickson |
| 5,551,419 | 9/1996 | Froehlich et al. |
| 5,551,418 | 9/1996 | Estes et al. |
| 5,558,099 | 9/1996 | Bowman et al. |
| 5,567,127 | 10/1996 | Wentz |
| 5,570,682 | 11/1996 | Johnson |

UNITED STATES PATENT AND TRADEMARK OFFICE
CERTIFICATE OF CORRECTION

PATENT NO. : 6,571,599 B1
DATED : June 3, 2003
INVENTOR(S) : Surjadi et al.

Page 4 of 8

It is certified that error appears in the above-identified patent and that said Letters Patent is hereby corrected as shown below:

Title page (cont'd),

| | | |
|---|---|---|
| 5,588,439 | 12/1996 | Hollub |
| 5,598,838 | 2/1997 | Servidio et al. |
| 5,605,151 | 2/1997 | Lynn |
| 5,608,647 | 3/1997 | Rubsamen et al. |
| 5,617,846 | 4/1997 | Graetz et al. |
| 5,630,411 | 5/1997 | Holscher |
| 5,632,269 | 5/1997 | Zdrojkowski |
| 5,633,552 | 5/1997 | Lee et al. |
| 5,642,730 | 7/1997 | Baran |
| 5,645,053 | 7/1997 | Reemers et al. |
| 5,645,054 | 7/1997 | Cotner et al. |
| 5,647,351 | 7/1997 | Weismann et al. |
| 5,655,520 | 8/1997 | Howe et al. |
| 5,655,522 | 8/1997 | Mechlenburg et al. |
| 5,660,171 | 8/1997 | Kimm et al. |
| 5,666,946 | 9/1997 | Langenback |
| 5,682,878 | 11/1997 | Ogden |
| 5,685,296 | 11/1997 | Zdrojkowski et al. |
| 5,701,883 | 12/1997 | Hete et al. |
| 5,704,345 | 1/1998 | Berthon-Jones |
| 5,715,812 | 2/1998 | Deighan et al. |
| 5,730,121 | 3/1998 | Hawkins |
| 5,740,795 | 4/1998 | Brydon |
| 5,794,615 | 8/1998 | Estes |
| 5,797,852 | 8/1998 | Karakasoglu et al. |
| 5,803,066 | 9/1998 | Rapoport et al. |
| 5,823,187 | 10/1998 | Estes et al. |
| 5,845,636 | 12/1998 | Gruenke et al. |
| 5,928,156 | 7/1999 | Krumbiegel et al. |

FOREIGN PATENT DOCUMENTS

| | | |
|---|---|---|
| AU | B-59270/90 | 12/1990 |
| AU | A-62221/90 | 3/1991 |
| AU | A-33877/93 | 4/1993 |
| AU | A-38508/93 | 7/1993 |
| AU | A-48748/93 | 12/1993 |
| AU | A-52628/93 | 7/1994 |
| AU | B 79174/94 | 6/1995 |
| AU | A-39130/95 | 6/1996 |
| AU | A-42027/97 | 2/1998 |
| AU | B-34354/95 | 5/1996 |
| AU | A-34471/95 | 2/1996 |
| AU | A-40711/95 | 4/1996 |
| DE | 459 104 | 4/1928 |
| DE | 296 12 119 U1 | 12/1996 |
| DE | 3015279 A1 | 10/1981 |
| DE | 3345067 A1 | 6/1984 |
| DE | 3402603 A1 | 1/1984 |
| DE | 3429345 A1 | 6/1984 |
| DE | 3537507 A1 | 4/1987 |
| DE | 3539073 A1 | 5/1987 |
| DE | 4432219 C1 | 4/1996 |
| EP | 0 062 166 A2 | 10/13/82 |
| EP | 0 066 451 A1 | 12/1982 |
| EP | 0 088 761 B1 | 9/1983 |
| EP | 0 164 500 A2 | 3/1985 |
| EP | 0 171 321 A1 | 2/1986 |
| EP | 0 178 925 A2 | 4/1996 |
| EP | 0 185 980 | 7/1986 |
| EP | 0 236 850 A2 | 9/1987 |
| EP | 0 298 367 A2 | 1/1989 |

UNITED STATES PATENT AND TRADEMARK OFFICE
CERTIFICATE OF CORRECTION

PATENT NO.    : 6,571,599 B1
DATED         : June 3, 2003
INVENTOR(S)   : Surjadi et al.

It is certified that error appears in the above-identified patent and that said Letters Patent is hereby corrected as shown below:

<u>Title page (cont'd)</u>,

| | | |
|---|---|---|
| EP | 0 388 525 A1 | 9/1990 |
| EP | 0 425 092 A1 | 5/1991 |
| EP | 0 452 001 A2 | 3/1990 |
| EP | 0 461 281 A1 | 12/1991 |
| EP | 0 481 459 A1 | 4/1992 |
| EP | 0 549 299 A2 | 6/1993 |
| EP | 0 606 687 A2 | 7/1994 |
| EP | 0 651 971 A1 | 5/1995 |
| EP | 0 656 216 A2 | 6/1995 |
| EP | 0 661 071 A1 | 7/1995 |
| EP | 0 705 615 A1 | 9/1994 |
| EP | 0 709 107 A1 | 5/1996 |
| EP | 0 714 670 A2 | 6/1996 |
| EP | 0 765 631 A2 | 4/1997 |
| EP | 0 788 805 A2 | 8/1997 |
| EP | 0 839 545 A1 | 5/1998 |
| EP | 0 872 643 A2 | 10/1998 |
| FR | 2 574 657 A1 | 6/1986 |
| FR | 2 682 042 A1 | 4/1993 |
| FR | 2 672 221 A1 | 8/1992 |
| GB | 1 432 571 | 4/1976 |
| GB | 1 444 053 | 7/1976 |
| GB | 1 583 273 | 1/1981 |
| GB | 2 077 444 A | 12/1981 |
| GB | 2 147 506 A | 5/1985 |
| GB | 2 164 569 A | 3/1986 |
| GB | 2 166 871 A | 5/1986 |
| GB | 2 205 167 A | 11/1988 |
| GB | 2 221 302 A | 1/1990 |
| GB | 2 254 700 | 10/1992 |
| GB | 2 261 290 A | 5/1993 |
| GB | 2 271 811 A | 4/1994 |
| GB | 2 294 400 A | 5/1996 |
| JP | 54-104365 | 3/1978 |
| JP | 54-104366 | 3/1978 |
| JP | 54-104369 | 8/1978 |
| JP | 60-212607 | 10/1985 |
| JP | 62-103297 | 4/1987 |
| JP | 63-275352 | 11/1988 |
| JP | 2-173397 | 12/1988 |
| JP | 4-70516 A | 3/1992 |
| JP | 06249741 A | 9/1994 |
| JP | 6-249742 A | 9/1994 |
| JP | 07280609 A | 10/1995 |
| JP | 8019610 A | 1/1996 |
| SE | 467041 B | 5/1992 |
| SU | 1710064A1 | 2/1992 |
| WO | 80/01044 | 5/1980 |
| WO | 82/03326 | 10/1982 |
| WO | 82/03548 | 10/1982 |
| WO | 86/05965 | 10/1986 |
| WO | 86/06969 | 12/1986 |
| WO | 87/02577 | 5/1987 |
| WO | 88/10108 | 12/1988 |
| WO | 90/14121 | 1/1990 |
| WO | 91/12051 | 8/1991 |
| WO | 92/11054 | 7/1992 |
| WO | 92/22244 | 12/1992 |
| WO | 92/15353 | 9/1992 |
| WO | 93/08857 | 5/1993 |
| WO | 93/09834 | 5/1993 |

UNITED STATES PATENT AND TRADEMARK OFFICE
CERTIFICATE OF CORRECTION

PATENT NO.    : 6,571,599 B1
DATED         : June 3, 2003
INVENTOR(S)   : Surjadi et al.

It is certified that error appears in the above-identified patent and that said Letters Patent is hereby corrected as shown below:

<u>Title page (cont'd),</u>

| | | |
|---|---|---|
| WO | 93/21982 | 11/1993 |
| WO | 93/24169 | 12/1993 |
| WO | 94/04071 | 3/1994 |
| WO | 94/16759 | 8/1994 |
| WO | 94/20018 | 9/1994 |
| WO | 94/20051 | 9/1994 |
| WO | 94/23780 | 10/1994 |
| WO | 95/32016 | 11/1995 |
| WO | 96/16688 | 6/1996 |
| WO | 96/32055 | 10/1996 |
| WO | 96/36279 | 11/1996 |
| WO | 96/40337 | 12/1996 |
| WO | 96/41571 | 12/1996 |
| WO | 97/02064 | 1/1997 |
| WO | 97/05824 | 2/1997 |
| WO | 97/10019 | 3/1997 |
| WO | 97/10868 | 3/1997 |
| WO | 97/15343 | 5/1997 |
| WO | 97/18752 | 5/1997 |
| WO | 97/20499 | 6/1997 |
| WO | 97/22377 | 6/1997 |
| WO | 97/28838 | 8/1997 |
| WO | 97/41812 | 11/1997 |
| WO | 98/06449 | 2/1998 |
| WO | 98/25662 | 6/1998 |
| WO | 98/33433 | 8/1998 |
| WO | 98/35715 | 8/1998 |
| WO | 98/36245 | 8/1998 |
| WO | 98/36338 | 8/1998 |
| WO | 98/47554 | 10/1998 |
| WO | 98/57691 | 12/1998 |

OTHER PUBLICATIONS

New! Breas PV 100 CPAP First Class Quality and Function. At the right Price; 07/04/98, pp 102

PV 101 Bi Level CPAP and PV 102 Bi-Level Time; pp 1-3

Prodigy Medical Supplies Co. Ltd.; CPAP

Puritan Bennett; Companion 318 Nasal CPAP System; 5/93

Nellcor Puritan Bennett; Announcing the Goodnight 314 and GoodKnight 318 Nasal CPAP Systems Puritan Bennett; Clean, Quiet, and Comfortable... The Companion's 515 Nasal CPAP System; 6/88

DeVilbiss Night Guard Nasal CPAP for the Treatment of Obstructive Sleep Apnea

Sunrise; DeVilbiss Horizon LT 8001 Nasal CPAP Therapy Small in Size, big features DeVilbiss; Revitalizer Soft Start; The Facts Speak for Themselves Tranquility; Performance CPAP Advantage Healthdyne International; Tranquility Plus Respironics Inc.; Respironics' Solo CPAP System Provides Simplified OSA Therapy at an Outstanding value; 9/19/96

Respironics Inc.; The First Family of OSA Therapy; 1991

Fisher & Paykel Healthcare; HC200 Series Nasal CPAP Blower & Heated Humidifier

Pierre Medical; Morphee Plus appareil de traitment des apnees du sommeil manuel d'utilisation

UNITED STATES PATENT AND TRADEMARK OFFICE
CERTIFICATE OF CORRECTION

PATENT NO.   : 6,571,599 B1
DATED        : June 3, 2003
INVENTOR(S)  : Surjadi et al.

It is certified that error appears in the above-identified patent and that said Letters Patent is hereby corrected as shown below:

Title page (cont'd),

Weinmann-Hamburg; Somnotron nCPAP-Great WM 2300

Puritan Bennett; 515a Part of Our Blueprint for the Future; 03/90

Puritan Bennett; Companion 320 I/E Bi-Level Respiratory System; 4/93

ResMed; Sullivan VPAP II & II ST

ResMed; The Sullivan V Family of CPAP Systems

ResMed; The AutoSet Portable II

ResMed: Sullivan Nasal CPAP System

ResMed; The Sullivan IIID

ResMed; The Sullivan Comfort

DeVilbiss a Division of Sunrise Medical; Expand your Horizons With The Horizons

Healthdyne Technologies; Home Health Care Dealer; The Journal of Home Medical Equipment and Services/Supplier; November and December 1997

Healthdyne International; Tranquility Quest, The Compact CPAP for Greater patient comfort Air Step; Medical Products... Stand the Test of Time MAP Medical Progress for Physician and Patient; The Gentle Therapy for Sleep-Related Breathing Disorders

UNITED STATES PATENT AND TRADEMARK OFFICE
CERTIFICATE OF CORRECTION

PATENT NO. : 6,571,599 B1
DATED : June 3, 2003
INVENTOR(S) : Surjadi et al.

It is certified that error appears in the above-identified patent and that said Letters Patent is hereby corrected as shown below:

<u>Title page (cont'd),</u>

Taema; Ventilation CP 90

DPAP; Breath, by breath, by breath

Lifecare; Smallest. Quietest. Smartest.

Lifecare; Quiet CPAP System for Maximum Compliance; 1991

Lifecare; Software Nasal Mask, Custom Nasal Masks; 1991

Nidek Medical; Silenzio

Weinmann; Just to Fell Well, Sensitive Sleep Apnoea Therapy with Somnotron 3 and Somno-Mask System Respironics Inc.; Aria CPAP System Respironics Inc.; SleepEasy III A New Dawn in Patient Compliance Respironics Inc.; Multiple Choice REMstar Choice Nasal CPAP System MaxII nCPAP and Moritz II Bi-Level Brochure Derwent: Flowmeter for fluids-has turbine transducer and volumetric sensor for a simultaneous calibration Mark Kantrowitz, Erik Horskotte and Cliff Joslyn; "Answers to Frequently Asked Questions about Fuzzy Logic and Fuzzy Expert Systems" Version 1.24 last Modified 20 2 96

Signed and Sealed this

Fourth Day of January, 2005

JON W. DUDAS
*Director of the United States Patent and Trademark Office*